US009138745B2

(12) United States Patent
Momose

(10) Patent No.: US 9,138,745 B2
(45) Date of Patent: Sep. 22, 2015

(54) MICROCHIP

(71) Applicant: Rohm Co., Ltd., Kyoto (JP)

(72) Inventor: Shun Momose, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 80 days.

(21) Appl. No.: 13/762,522

(22) Filed: Feb. 8, 2013

(65) Prior Publication Data

US 2013/0209329 A1 Aug. 15, 2013

(30) Foreign Application Priority Data

Feb. 9, 2012 (JP) .................................. 2012-26005

(51) Int. Cl.
*B01L 3/00* (2006.01)
*G01N 21/07* (2006.01)
*G01N 33/48* (2006.01)

(52) U.S. Cl.
CPC ....... *B01L 3/50273* (2013.01); *B01L 3/502746* (2013.01); *B01L 3/502707* (2013.01); *B01L 3/502753* (2013.01); *B01L 3/502761* (2013.01); *B01L 2300/0816* (2013.01); *B01L 2300/0819* (2013.01); *B01L 2300/0864* (2013.01); *B01L 2300/0867* (2013.01); *B01L 2400/0409* (2013.01); *B01L 2400/086* (2013.01)

(58) Field of Classification Search
USPC ................................. 422/502–506, 527, 533
See application file for complete search history.

(56) References Cited

U.S. PATENT DOCUMENTS

| | | | | |
|---|---|---|---|---|
| 7,150,812 | B2 * | 12/2006 | Huang et al. | 204/451 |
| 7,195,872 | B2 * | 3/2007 | Agrawal et al. | 435/287.2 |
| 7,276,170 | B2 * | 10/2007 | Oakey et al. | 210/767 |
| 2003/0044322 | A1 * | 3/2003 | Andersson et al. | 422/100 |
| 2004/0121454 | A1 * | 6/2004 | Jury et al. | 435/288.5 |
| 2006/0035386 | A1 * | 2/2006 | Hattori et al. | 436/514 |
| 2007/0161051 | A1 * | 7/2007 | Tsinberg et al. | 435/7.2 |
| 2008/0290037 | A1 * | 11/2008 | Liu | 210/695 |

FOREIGN PATENT DOCUMENTS

| | | | | |
|---|---|---|---|---|
| EP | 1669733 A1 * | 6/2006 | | G01N 1/10 |
| JP | 2005-103423 | 4/2005 | | |
| JP | 2005-164242 | 6/2005 | | |
| JP | 2007-285792 | 11/2007 | | |

OTHER PUBLICATIONS

De Gennes et al., “Physics of Surface Tension,” p. 223 (2003), with English translation.

* cited by examiner

*Primary Examiner* — Jennifer Wecker
(74) *Attorney, Agent, or Firm* — Fish & Richardson P.C.

(57) ABSTRACT

A microchip which includes a fluid circuit defined by a space formed in the microchip and migrates a liquid present in the fluid circuit to a desired position in the fluid circuit by an applied centrifugal force, and a movement path control region (a surface region where an uneven pattern is formed on an inner surface of the fluid circuit) for controlling a movement path of the fluid.

10 Claims, 11 Drawing Sheets

MICROCHIP

CROSS-REFERENCE TO RELATED APPLICATION

This application is based upon and claims the benefit of priority from Japanese Patent Application No. 2012-26005, filed on Feb. 9, 2012, the entire contents of which are incorporated herein by reference.

TECHNICAL FIELD

The present disclosure relates to a microchip useful for a μ-TAS (Micro Total Analysis System) that may be used for biochemical examination on DNA (Deoxyribo Nuclear Acid), proteins, cells, immunity, blood, etc., chemical synthesis, environmental analysis or the like.

BACKGROUND

Recently, it has become more important to sense, detect, or determine the quantity of biological materials such as DNAs, enzymes, antigens, antibodies, protein, viruses or cells or chemical materials in the field of medical treatment, health, foods and drug development or the like, and various biochips and micro chemical chips (hereinafter collectively referred to as "microchips") have been proposed which can measure the biological materials easily.

With the microchip, a series of examination and analysis operations conventionally performed in laboratories may be performed in the small chip. Thus, on-chip detection has many advantages in that the examination and analysis may be performed with a small amount of specimen and liquid reagent, but at low cost, with a fast reaction rate, and high throughput, and results of the examination and analysis may be obtained immediately when the specimen is collected.

In the related art, a microchip is known, which includes a plurality of portions (chambers) for carrying out specific treatments for liquid such as a specimen or liquid reagent present in the so-called fluid circuit (or a micro fluid circuit) and a flow path network consisting of fine flow paths which connect the portions properly. In the examination or analysis on the specimen using the microchip having therein such a fluid circuit, various processes such as measuring the specimen introduced into the fluid circuit (or specific component in the specimen) or liquid reagents to be mixed therewith (by moving them to a measuring portion for performing the measuring), mixing the specimen (or a specific component in the specimen) with the liquid reagent (by moving them to a mixing portion for performing the mixing) portion, and moving the specimen or the liquid reagent from one portion to another portion are performed.

In addition, hereinafter, "fluid treatment" refers to a process performed for various liquids (such as the specimen, the specific component in the specimen, the liquid reagent, or a mixture of two or more thereof) in the microchip. These various fluid treatments can be performed by applying centrifugal force in an appropriate direction with respect to the microchip.

In order to perform a good control of the fluid treatment in the microchip, it is important to ensure the liquid in the fluid circuit is moved from one portion to another portion along a path as intended (as designed) when the centrifugal force is applied in a predetermined direction. If at least a portion of the liquid is not moved to a predetermined portion, thereby departing from the intended path, and moved elsewhere in the fluid circuit, a predetermined fluid treatment may not be properly performed. Thus, it is likely that the accuracy in the examination and analysis on the specimen is lowered or the examination and analysis itself may not be performed.

One of major factors which would cause the liquid in the fluid circuit to depart from the intended path at the application of the centrifugal force is a high wettability of the liquid with respect to an inner surface of the fluid circuit. When the liquid in the fluid circuit has a high wettability with respect to the inner surface of the fluid circuit, the liquid may be moved along an unintended path on account of the action of force causing the liquid to move along the side surface of the fluid circuit due to the high wettability, even though the centrifugal force is applied in a predetermined direction so as to move the liquid along the predetermined path.

In order to solve the problem as described above, a technique is known in the related art which reduces the wettability of the liquid with respect to the inner surface of the fluid circuit by applying a water-repellent agent on the inner surface of the fluid circuit. However, the method complicates a manufacturing process of the microchip, thus reducing production efficiency significantly. In addition, it is difficult to control the wettability of the liquid with respect to the inner surface for only a portion of the fluid circuit.

SUMMARY

The present disclosure provides some embodiments of a microchip which can ensure liquid in a fluid circuit is moved along an intended path in response to the application of a centrifugal force, while achieving improved manufacturability at the same time.

According to some embodiments, a microchip includes a fluid circuit defined by a space formed in the microchip and is configured to move a liquid present in the fluid circuit to a desired position in the fluid circuit by applying a centrifugal force. The microchip includes a movement path control region having an uneven pattern that controls a movement path of the fluid on an inner surface of the fluid circuit.

When the liquid is moved from a region A to a region B within the fluid circuit by the application of the centrifugal force, the movement path control region may be provided so as to include at least a portion of a region interposed between the region A and the region B. In addition, the movement path control region may be provided on a bottom surface of the fluid circuit.

In one embodiment, the uneven pattern in the movement path control region includes a plurality of linear protrusions arranged in parallel at intervals. In this case, the angle between a direction in which the centrifugal force is applied in order to move the fluid and a longitudinal direction of the linear protrusions may be more than 0 degrees but less than 90 degrees.

In another embodiment, the uneven pattern in the movement path control region includes a plurality of columnar protrusions arranged at intervals vertically and horizontally. Further, in another embodiment, the uneven pattern in the movement path control region includes a plurality of trenches arranged at intervals vertically and horizontally so as to surround a portion of the inner surface of the fluid circuit.

DETAILED DESCRIPTION

Reference will now be made in detail to various embodiments, examples of which are illustrated in the accompanying drawings. In the following detailed description, numerous specific details are set forth in order to provide a thorough understanding of the present invention(s). However, it will be apparent to one of ordinary skill in the art that the present invention(s) may be practiced without these specific details. In other instances, well-known methods, procedures, systems, and components have not been described in detail so as not to unnecessarily obscure aspects of the various embodiments.

Figure 1:
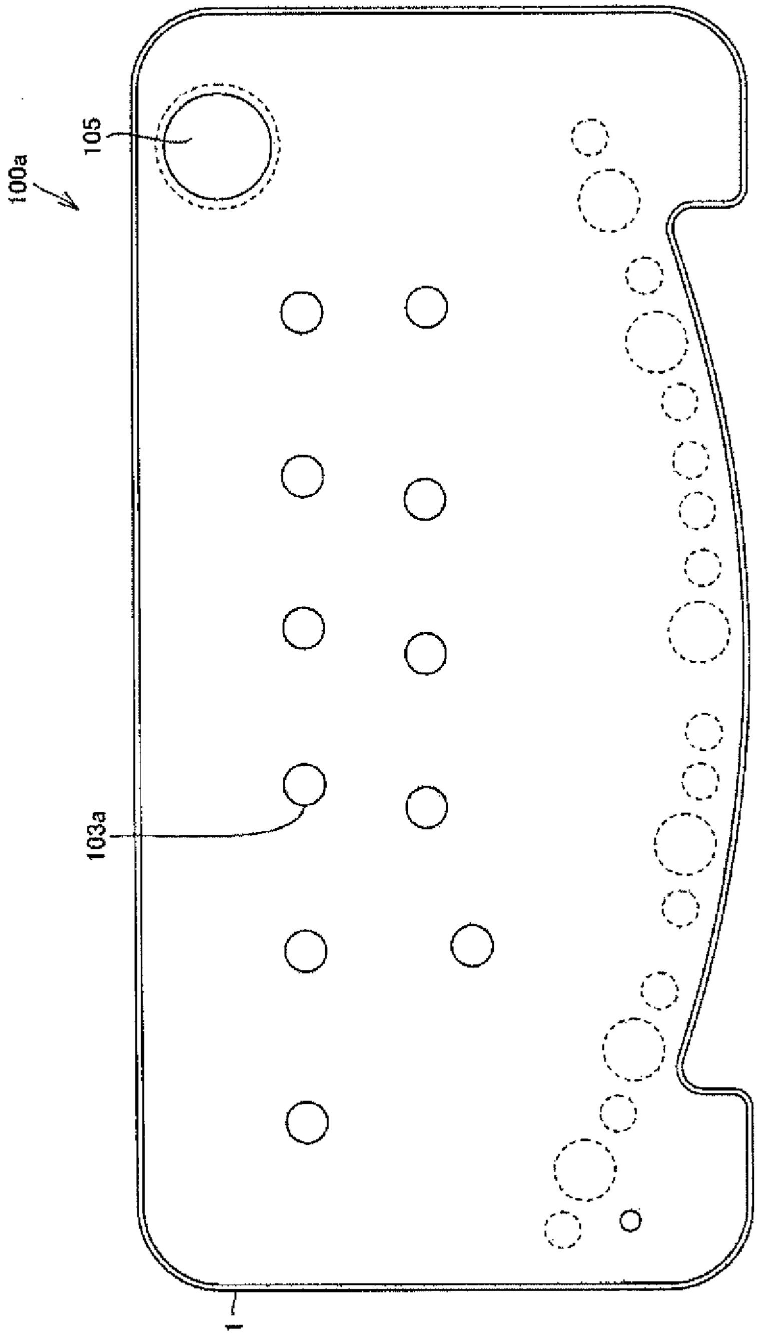
FIG. 1 is a top view of a microchip when viewed from a first substrate side, according to some embodiments.
Figure 2:
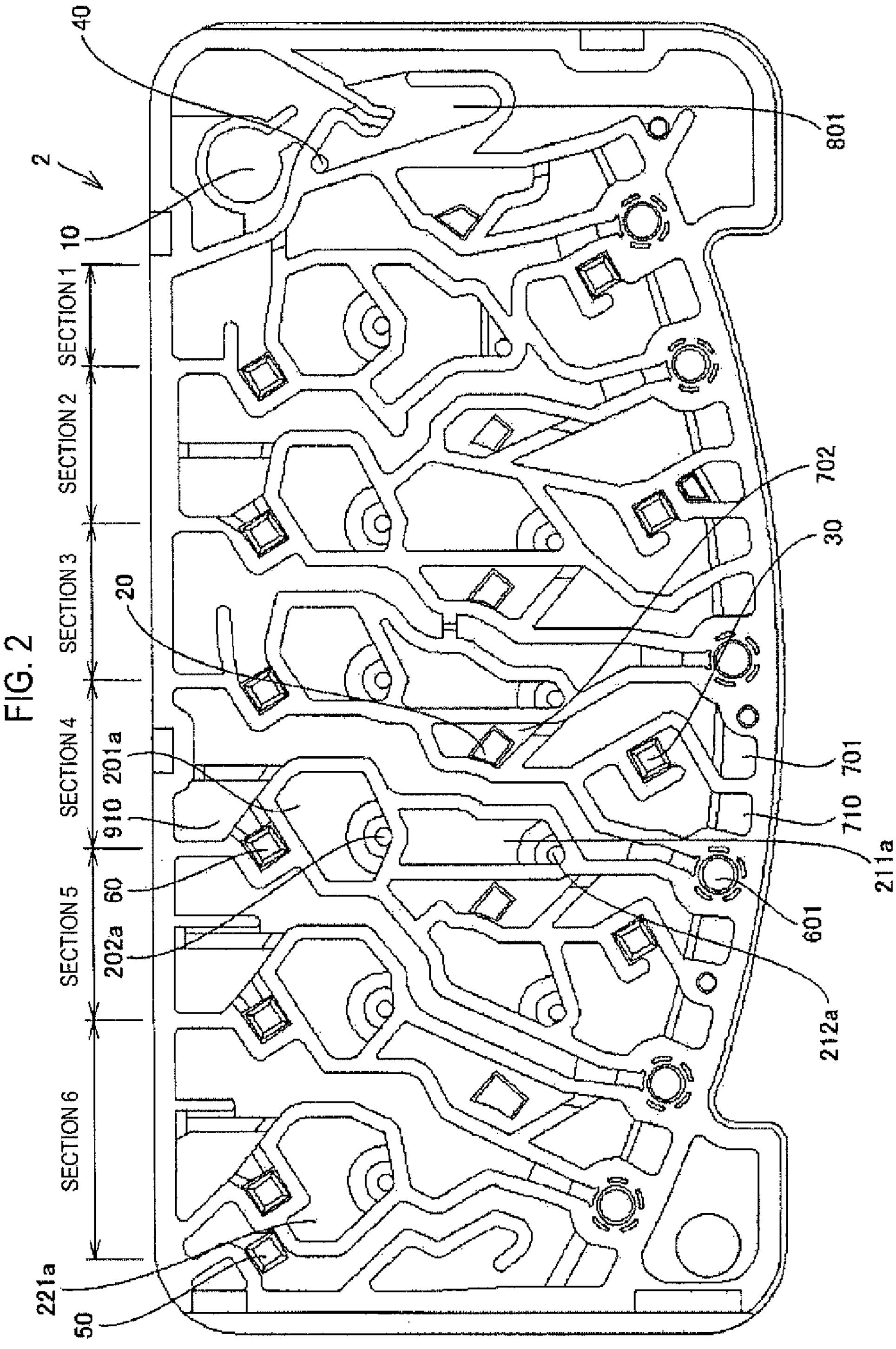
FIG. 2 is a top view showing a surface of a second substrate constituting a microchip on a first substrate side, according to some embodiments.
Figure 3:
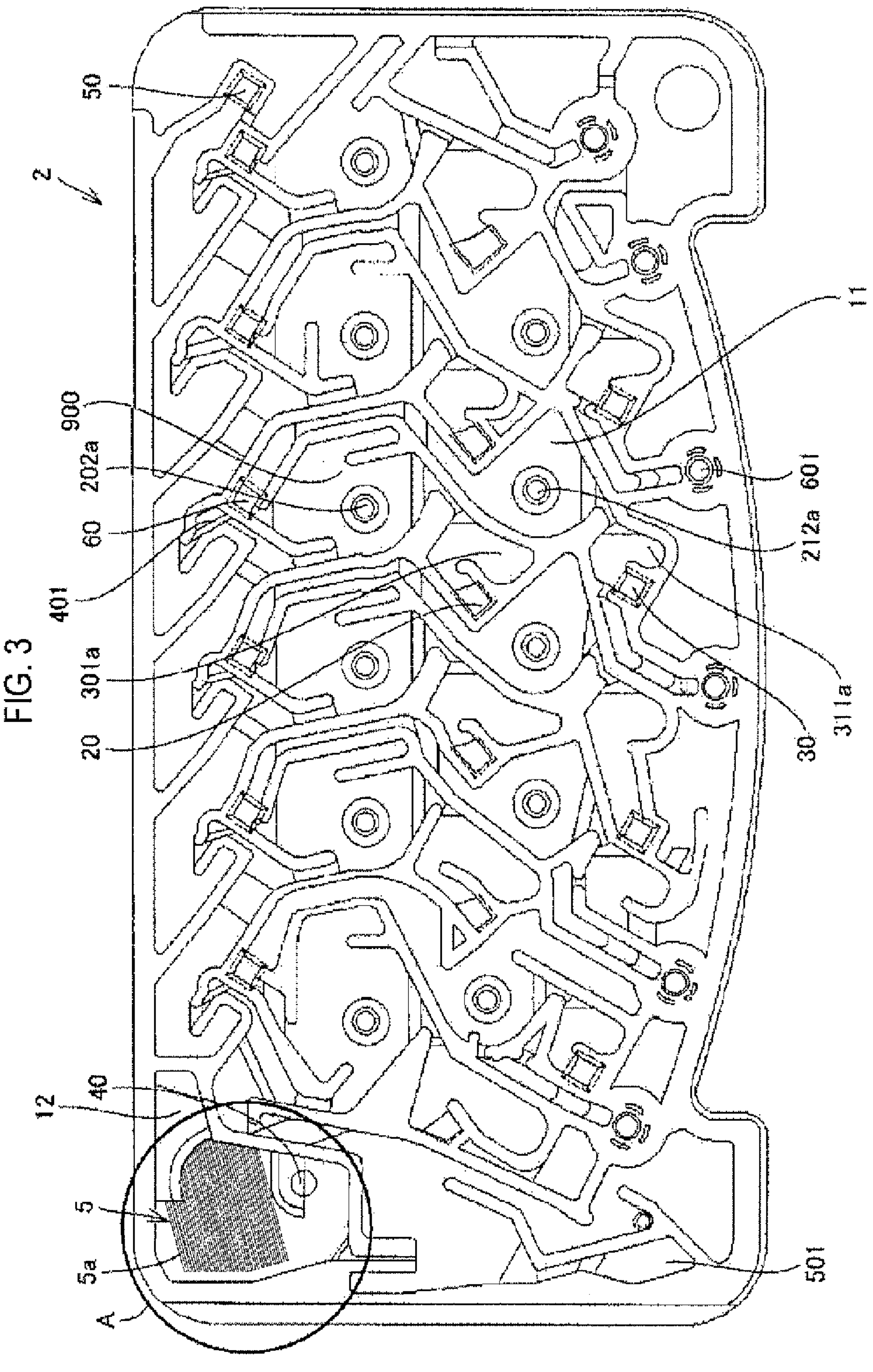
FIG. 3 is a top view showing a surface of a second substrate constituting a microchip on a third substrate side, according to some embodiments.
Figure 4:
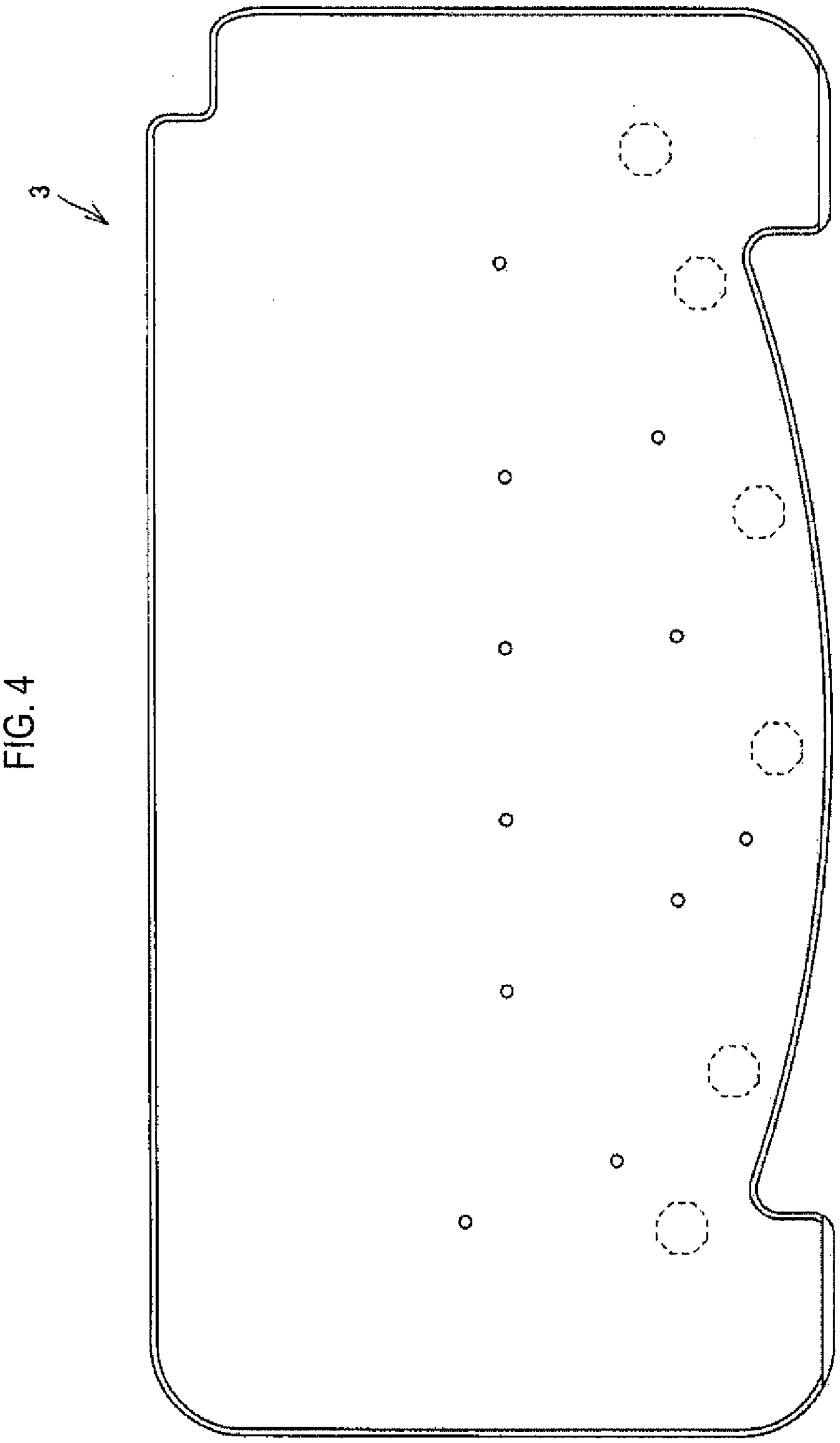
FIG. 4 is a top view showing an outer surface of a third substrate constituting a microchip, according to some embodiments.

FIGS. 1 to 4 show an embodiment (hereinafter, referred to as Embodiment I) of a microchip 100*a* and substrates constituting the microchip 100*a*. The microchip 100*a* shown in FIGS. 1 to 4 is formed by stacking and bonding a first substrate 1 which is a transparent substrate, a second substrate 2 which is a black substrate having grooves forming the fluid circuit on its both surfaces, and a third substrate 3 which is a transparent substrate in this order. FIG. 1 is a top view of the microchip 100*a* when viewed from a direction of the first substrate 1. FIG. 2 is a top view showing a surface of the second substrate 2 facing the first substrate 1, and FIG. 3 is a top view showing a surface of the second substrate 2 facing the third substrate 3. FIG. 4 is a top view of an outer surface of the third substrate 3 (the surface on the opposite side with respect to the second substrate 2). In addition, dotted-lines in FIGS. 1 and 4 mean that regions surrounded by the dotted-lines are concave portions.

The microchip 100*a* includes a fluid circuit formed therein (a space formed therein), in which various chemical syntheses, examinations or analyses are performed. The microchip 100*a* can perform fluid treatments on a liquid (a specimen, a specific component in the specimen, a reagent such as a liquid reagent, and a mixture of two or more thereof) properly by moving the liquid to a predetermined location (portion) in the fluid circuit by applying a centrifugal force. The fluid circuit includes various portions (chambers) placed in predetermined positions, and the portions may be connected through fine flow paths.

The various portions (chambers) in the fluid circuit may include: a reagent retaining portion 201*a* and 211*a* for receiving a liquid reagent to be mixed with (or reacted with) a specimen to be examined or analyzed; a separation portion 501 for extracting a specific component from the specimen introduced into the fluid circuit; a specimen measuring portion 401 for measuring the specimen (or the specific component in the specimen; the same shall apply hereinafter); a reagent measuring portion 301*a* or 311*a* for measuring the liquid reagent; a mixing portion 900 or 910 for mixing the specimen and the liquid reagent; a detection portion 601 for performing an examination or an analysis on a resultant mixed liquid (for example, detection or quantification of a specific component in the mixed liquid); a excess liquid storing portion 701 or 710 for receiving an excess liquid (for example, a specimen or a liquid reagent overflowing out of the specimen measuring portion 401 or the reagent measuring portion 301*a* or 311*a* during the measuring); a receiving portion 801 for receiving a specific liquid temporarily, and so forth.

Typically, the microchip 100*a* includes, on its one surface, a reagent inlet (penetrating to the reagent retaining portion 201*a* and 211*a*) 103*a* for injecting the liquid reagent into the reagent retaining portion 201*a* or 211*a*. The reagent inlet 103*a* is sealed by bonding a sealing layer (not shown) such as a label (seal) for sealing on the surface of the microchip 100*a* after the injection of the liquid reagent. In addition, the microchip 100*a* includes, on its surface, a specimen inlet (penetrating to the fluid circuit and being connected thereto) 105 for injecting the specimen for examination or analysis.

The method of inspecting or analyzing the mixed liquid introduced into the detection portion 601 is not particularly limited, but may be, for example, an optical measurement such as a method of irradiating the detection portion receiving the mixed liquid with light and detecting an intensity of transmitted light (transmittance), a method of measuring an absorption spectrum for the mixed liquid retained by the detection portion, and so forth.

The microchip 100*a* may have all the portions (chambers) as described above and may not have any one or more of the portions. In addition, the microchip 100*a* may have other portions than the described portions. There is no particular limitation on the number of each portion, and one or more of each portion may exist.

Various fluid treatments such as extracting the specific component from the specimen (separation of unnecessary component), measuring the specimen and the liquid reagent, mixing the specimen with the liquid reagent, and introducing the resultant mixed liquid into the detection portion may be performed by applying centrifugal forces sequentially in appropriate directions with respect to the microchip 100*a* and moving the target liquid sequentially to predetermined portions placed in predetermined positions. For example, measuring of the specimen and measuring of the liquid reagent by the measuring portions may be carried out, respectively, by introducing the specimen or the liquid reagent (to be measured) to the specimen measuring portion 401 or the reagent measuring portion 301*a* or 311*a* having a predetermined capacity (an amount to be measured) by applying a centrifugal force and making an excess of the specimen or the liquid reagent overflow out of the specimen measuring portion 401 or the reagent measuring portion 301*a* or 311*a*. The overflown specimen or liquid reagent can be received in the excess liquid storing portion 701 or 710 connected to the specimen measuring portion 401 or the reagent measuring portion 301*a* or 311*a* through the flow path.

The centrifugal force can be applied to the microchip 100*a* by mounting the microchip 100*a* on a centrifugal device (not shown) which can apply the centrifugal force. The centrifugal device may include a rotatable rotor (rotator) and a rotatable stage placed on the rotor. The centrifugal force can be applied in any direction with respect to the microchip by mounting the microchip on the stage, rotating the stage to set an angle of the microchip with respect to the rotor arbitrarily, and then rotating the rotor.

The microchip 100*a* may include a first substrate 1 and a second substrate 2 stacked on and bonded to the first substrate 1. More specifically, the second substrate 2 having grooves on its surface can be bonded to the first substrate 1, with the surface having the grooves facing the first substrate 1. The microchip 100*a* consisting of these two substrates 1 and 2 includes a fluid circuit defined by an inner space formed by the surface of the first substrate 1 facing the second substrate 2 and the grooves provided on the surface of the second substrate 2.

In addition, the microchip 100*a* may be formed by stacking a first substrate 1, a second substrate 2 having grooves on both its surfaces, and a third substrate 3 in this order. The microchip 100*a* consisting of these three substrates 1, 2 and 3 includes two layers of fluid circuits: a first fluid circuit defined by an inner space formed by the surface of the first substrate 1 facing the second substrate 2 and the groove provided on the surface of the second substrate 2 facing the first substrate 1, and a second fluid circuit defined by an inner space formed by the surface of the third substrate 3 facing the second substrate 2 and the groove provided on the surface of the second substrate 2 facing the third substrate 3. The term "two layers" means that fluid circuits are provided in two different positions with respect to the thickness direction of the microchip 100*a*. These two layers of fluid circuits may be connected by one or more through-holes (for example, through-holes 20, 30, 40, 50 and 60) penetrating the second substrate 2 in the thickness direction.

The method of bonding substrates 1, 2 and 3 together is not particularly limited, but may include, for example, a method of welding by melting the bonding surface of at least one of substrates to be bonded (welding method), a method of bonding using an adhesive, and so forth. The welding method may include a method of welding by heating the substrate, a method of welding using heat generated when light absorption occurs by irradiating with light such as laser (laser welding), a method of welding using ultrasonic wave, and so forth. Among these, the laser welding may be used.

The size of the microchip 100*a* is not particularly limited, but may be, for example, about several centimeters in both length and width and about several millimeters to 1 cm in thickness.

The material of each of the substrates 1, 2 and 3 as mentioned above constituting the microchip 100*a* is not particularly limited, but may be, for example, formed of thermoplastic resin such as polyethylene terephthalate (PET), polybutylene terephthalate (PBT), polymethyl methacrylate (PMMA), polycarbonate (PC), polystyrene (PS), polypropylene (PP), polyethylene (PE), polyethylene naphthalate (PEN), polyarylate resin (PAR), acrylonitrile-butadiene-styrene resin (ABS), polyvinyl chloride resin(PVC), polymethyl pentene resin (PMP), polybutadiene resin (PBD), biodegradable polymer (BP), cyclo-olefin polymer (COP), polydimethylsiloxane (PDMS), and so forth.

When the microchip 100*a* includes the first substrate 1 and the second substrate 2 having grooves on its surface, the second substrate 2 may be a transparent substrate so as to provide a detection portion (not shown) for an optical measurement using detected light. The first substrate 1 may be a transparent substrate or an opaque substrate. If the first substrate 1 is the opaque substrate, light absorption can be increased, in the case of performing the laser welding. The first substrate 1 may be a black substrate, which may be obtained by adding a black pigment such as carbon black to the above-mentioned thermoplastic resin.

When the microchip 100*a* includes the first substrate 1, the second substrate 2 having grooves on its both surfaces, and the third substrate 3, the second substrate 2 may an opaque substrate or a black substrate; of the type of substrate of may affect an efficiency of the laser welding. On the other hand, the first substrate 1 and the third substrate 3 may be transparent substrates so as to provide a detection portion (not shown) for the optical measurement using detected light. If the first substrate 1 and the third substrate 3 are transparent substrates, the detection portion for the optical measurement can be formed of the through-hole provided in the second substrate 2 and the transparent first substrate 1 and third substrate 3. In addition, it is possible to perform the optical measurement by irradiating the detection portion with light from a direction approximately perpendicular to the surface of the microchip 100*a* to detect intensity (transmittance) of transmitted light.

The method of forming the grooves (pattern grooves) for forming the fluid circuit on the surface of the second substrate 2 is not particularly limited, but may include a method of injection molding using a mold having a transcriptional structure, a method of imprinting, a method of cutting, and so forth. The shape and pattern of the grooves formed on the second substrate 2 are determined so that the inner space may be formed in a structure of a desired fluid circuit appropriately. In addition, the grooves for forming the fluid circuit may also be provided on substrates other than the second substrate 2 (i.e., on the first substrate 1 and/or the third substrate 3). Further, groove portions or concave portions may be formed on an outer surface of the first substrate 1 and the third substrate 3, and through-holes or the like may be provided in the first substrate 1 and the third substrate 3.

The microchip 100*a* having the structure as described above includes a movement path control region (a surface region where an uneven pattern is formed on the inner surface of the fluid circuit) for controlling the movement path of a liquid (a specimen, a specific component in the specimen, a reagent such as liquid reagent, or a mixture of two or more thereof) moving within the fluid circuit when centrifugal force is applied. In the case of moving the liquid by the application of centrifugal force, it is possible to control the movement path of the liquid properly so that the liquid may move along an intended path while preventing the liquid from moving along an unintended (not expected on design) path by providing the movement path control region in a region of the fluid circuit where paths different from the intended path (expected on design) may be erroneously taken (especially, on the inner surface of the region in the flow path connecting each portion (chamber)).

The fluid circuit of the microchip can be highly-integrated in order to realize miniaturization of the microchip. Thus, in general, the flow paths constituting the fluid circuit are complicated. Therefore, some flow paths for moving a liquid from a portion (chamber) to another portion may be disposed in close proximity to or connected to other flow paths. For example, if there is a flow path 'a' through which the liquid is moved from a region A to a region B in the fluid circuit and a flow path 'b' through which the fluid is led to another region C different from regions A and B is connected to the flow path 'a', a problem may be caused that at least a portion of the liquid deviates from the flow path 'a' and enters the flow path 'b', then is led to the region C, even when the centrifugal force is applied in a predetermined direction in order to move the liquid from the region A to the region B.

The movement path control region may include at least a portion of the region interposed between the region A and the region B (that is, at least a portion of the inner surface of the flow path 'a') and control (or regulate) the movement path of the liquid moving through the movement path control region, thus causing the liquid to move along the predetermined path in the flow path 'a' while preventing the liquid from entering the flow path 'b', even when the centrifugal force is applied in the same direction as that in the case where the problem as described above occurs.

Some embodiments of the microchip 100*a* will be described below in more detail.

The first substrate 1 will be described with reference to FIG. 1. The first substrate 1 includes a total of 11 reagent inlets including a reagent inlet 103*a*. The reagent inlets are through-holes penetrating the first substrate 1 in the thickness direction thereof, and are provided directly on and connected to each of 11 reagent retaining portions included in the fluid circuit, respectively. In addition, the first substrate 1 includes a specimen introduction hole 105 which is a through-hole penetrating the first substrate 1 in the thickness direction thereof for introducing the specimen (for example, whole blood) into the fluid circuit. The reagent inlet is sealed by bonding a sealing layer on the surface of the microchip 100*a* after the injection of the liquid reagent. The sealing layer may be a plastic film (such as a label, a seal, etc.) having an adhesive layer on one surface.

The fluid circuit of the microchip 100*a* will be described with reference to FIGS. 2 and 3. The second substrate 2 includes grooves formed on both its surfaces and a plurality of through-holes penetrating in the thickness direction, and two layers of fluid circuits are formed inside the microchip 100*a* by bonding the first substrate 1 and the third substrate 3 to the second substrate 2. In the following description, the fluid circuit formed by a surface of the first substrate 1 facing the second substrate 2 and grooves formed on the surface of the second substrate 2 facing the first substrate 1 is also referred to as "a first fluid circuit," and the fluid circuit formed by the surface of the third substrate 3 facing the second substrate 2 and grooves formed on the surface of the second substrate 2 facing the third substrate 3 is also referred to as "a second fluid circuit." These two fluid circuits are connected by several through-holes formed in and penetrating the second substrate 2 in the thickness direction thereof.

It is possible to understand a structure of the first fluid circuit with reference to FIG. 2 and a structure of the second fluid circuit with reference to FIG. 3. The microchip 100*a* of the present embodiment is a multiple item chip capable of examining/analyzing one specimen with regard to 6 items, and its fluid circuit is divided into 6 sections so that it can perform the examination/analysis with regard to 6 items. For example, the first fluid circuit is divided into sections 1 to 6 as shown in FIG. 2 and the same applies to FIG. 3(*the* second fluid circuit). These 6 sections are connected to each other in a region where the specimen measuring portion is formed (an upper region of the second fluid circuit shown in FIG. 3). In the following description, the "section 4" will be mainly described, since each of the above-mentioned sections has approximately the same configuration and is subject to the same fluid treatment.

In the section 4, the first fluid circuit includes two reagent retaining portions (reagent retaining portions 201*a* and 211*a* in FIG. 2) in which liquid reagent is contained. As described above, the reagent inlet (for example, the reagent inlet 103*a* in FIG. 1) which is a through-hole penetrating the first substrate 1 in the thickness direction thereof is provided in each reagent retaining portion. In addition, reagent exhaust passages 202*a* and 212*a* for exhausting the liquid reagent in the reagent retaining portions are, respectively, connected to a lower end of each reagent retaining portion (see FIG. 2). The reagent exhausting passages 202*a* and 212*a* are through-holes extending in the thickness direction of the second substrate 2 and are connected to the second fluid circuit. In FIG. 2, the liquid reagent exhausted from the reagent retaining portions 201*a* and 211*a* by the centrifugal force applied in a downward direction of FIG. 2 is introduced into each of reagent measuring portions 301*a* and 311*a* in the second fluid circuit, where the liquid reagent is measured (see FIG. 3). Here, the downward direction means that the direction of the centrifugal force applied to a center of the microchip is directed downward. For example, the downward direction in FIG. 2 refers to a downward direction when the drawing is placed such that a longitudinal end where a detection portion 601 is placed becomes a lower side and a longitudinal end opposite thereto becomes an upper side in the microchip shown in FIG. 2. The same applies to FIG. 3 and other directions other than the downward direction.

In the section 4, the second fluid circuit includes a specimen measuring portion 401 for measuring the specific component in the specimen. The specimen measuring portion is provided in each of 6 sections and connected to each other in series by the flow path (see FIG. 3).

In addition, the microchip 100*a* includes a separation portion 501 for extracting a specific component (a component to be mixed with the liquid reagent) out of the specimen introduced into the microchip 100*a* (see FIG. 3). For example, the separation portion 501 may separate a blood plasma component from a whole blood sample to get a blood cell component. The separating operation is performed by centrifugation.

The specimen introduced from the specimen introduction hole 105 is introduced into an receiving portion 801 through a region 10 by the application of centrifugal force in the downward direction of FIG. 2 (see FIG. 2), then introduced into a region 12 of the second fluid circuit through a through-hole 40 by the application of centrifugal force in a leftward direction of FIG. 2 (see FIG. 3). Subsequently, the specimen is introduced into the separation portion 501 by the application of the centrifugal force in the downward direction of FIG. 3, and then centrifuged (see FIG. 3).

The specific component of the specimen separated in the separation portion 501 is distributed to each section and measured in the specimen measuring portion (for example, the specimen measuring portion 401 in section 4), and mixed with one or two kinds of liquid reagent in each section, then introduced into corresponding detection portion (for example, the detection portion 601 in the section 4) (see FIGS. 2 and 3). For example, the mixed liquid introduced into the detection portion is subject to an optical measurement by irradiating the detection portion with detection light from a direction approximately perpendicular to the surface of the microchip 100*a* and measuring the transmittance of the transmitted light so that the specific component of the mixed liquid is detected.

Figure 5:
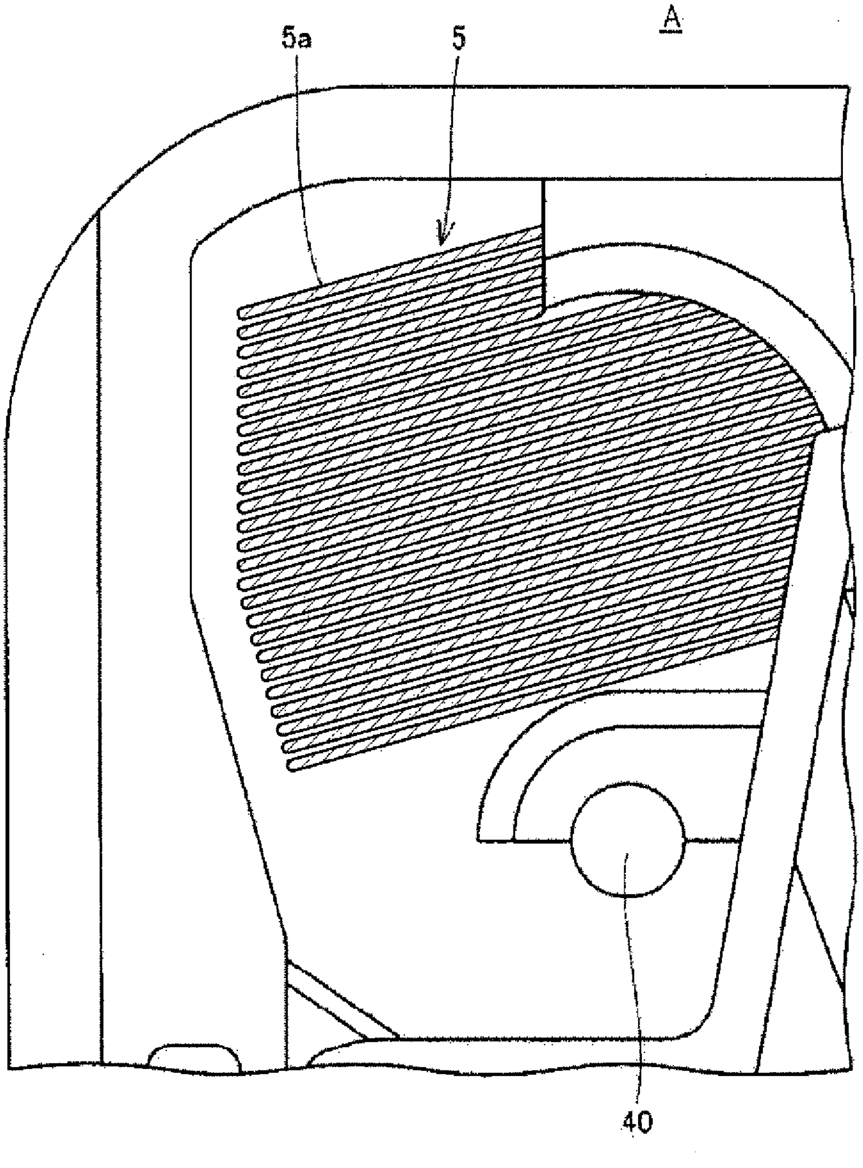
FIG. 5 is a top view showing an enlarged view of a portion "A" shown in FIG. 3.

With reference to FIG. 3 and FIG. 5 showing an enlarged view of the portion "A" shown in FIG. 3, the microchip 100_a_ includes a movement path control region 5 for controlling (e.g., regulating) the path when the specimen moves, on a portion of the inner surface of the flow path leading the specimen received in the region 12 to the separation portion 501. The movement path control region 5 is a surface region including an uneven pattern on a bottom surface of the flow path, that is, on the bottom surface of the groove formed on the surface of the second substrate 2 facing the first substrate 1. In this embodiment, the bottom surface of the flow path refers to a lower surface of the flow path when the microchip 100_a_ is placed on a stage of a centrifugal device for applying a centrifugal force during the examination and analysis, with the first substrate 1 being in an upper side.

The uneven pattern in the movement path control region 5 may include a plurality of linear protrusions 5_a_ arranged in parallel at intervals on the inner surface of the flow path. The linear protrusion 5_a_ has, for example, a width of 100 μm and a height of 50 μm. In addition, a pitch between the protrusions 5_a_ is, for example, 100 μm.

By providing the movement path control region 5, the microchip 100_a_ can properly control a movement path of the specimen when the specimen passes through the flow path connecting the region 12 and the separation portion 501 in case of moving the specimen from the region 12 to the separation portion 501 by the application of the centrifugal force, so as to prevent the specimen from flowing back to the through-hole 40 connected to the flow path. When the specimen is moved from the region 12 to the separation portion 501, a centrifugal force is applied in the downward direction of FIG. 3 (more specifically, in a bottom-left direction with respect to the portion "A") with respect to the microchip 100_a_ portion. However, a portion of the specimen may flow back to the through-hole 40 at the time of applying the centrifugal force when the movement path control region 5 is not provided, as described later. The movement path control region 5 provides a solution to such a problem and ensures that the total amount of specimen is reliably introduced into the separation portion 501.

The movement path control region 5 having the uneven pattern controls (modifies) the movement path of the liquid based on a principle that a contact angle of the liquid at a corner of the protrusion is larger than that at a flat portion of the surface of the protrusion (for example, see page 223 of "Physics of Surface Tension," co-authored by De Gennes, Brochard-Wyart, and Qu'er'e, translated by Tsuyoshi Okumura, issued in September 2003). When the contact angle at the flat portion of the surface of the protrusion is $\theta$ and an interior angle of the corner is x (degrees), the contact angle at the corner of the protrusion may be in a range of $\theta$ to $\theta+(180-x)$.

Figure 6A:
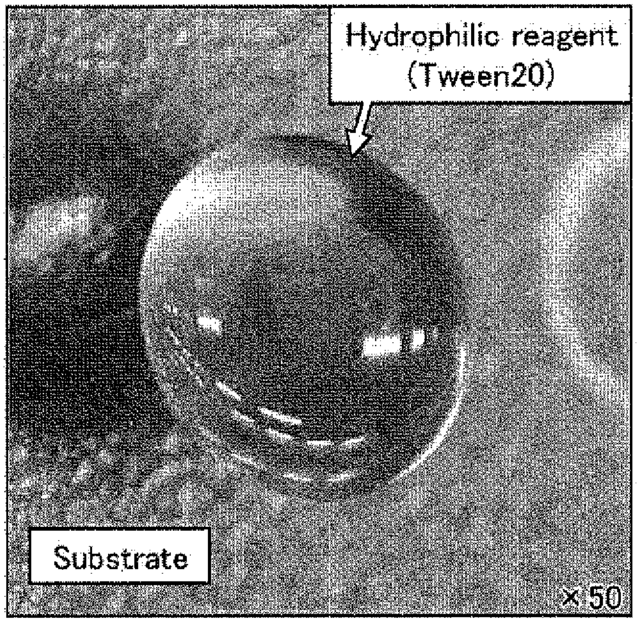
FIGS. 6A and 6B are photographic images showing a state when a droplet of hydrophilic reagent is placed on a flat substrate having no uneven pattern, according to some embodiments.
Figure 6B:
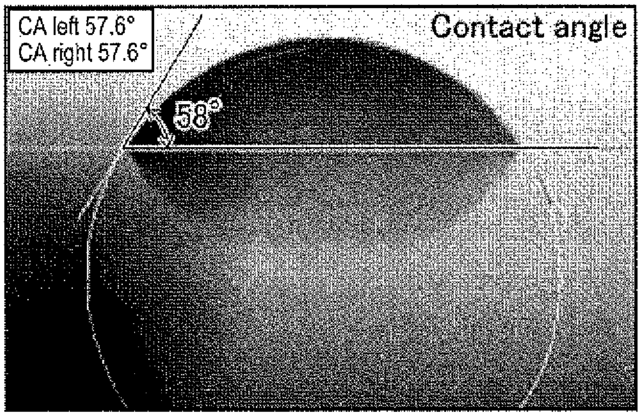
Figure 7A:
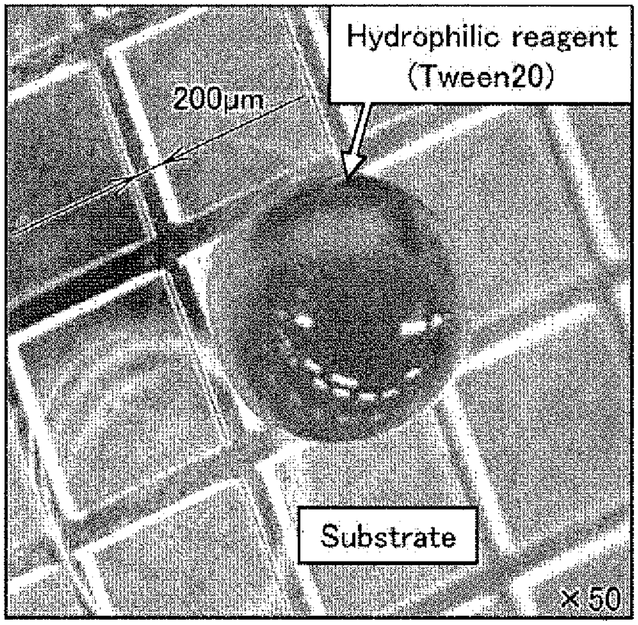
FIGS. 7A and 7B are photographic images showing a state when a droplet of hydrophilic reagent is placed on a substrate having an uneven pattern, according to some embodiments.
Figure 7B:
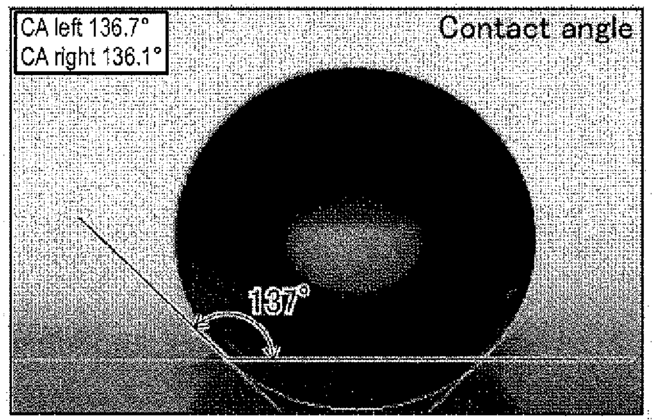

FIGS. 6A, 6B, 7A and 7B are photograph images showing experimental results which prove the above-mentioned function of the uneven pattern. FIGS. 6A and 6B are photographs showing a status of a droplet of hydrophilic reagent (aqueous reagent including surfactant Tween20) when placed on a flat substrate (not having the uneven pattern) formed of PMP (polymethyl pentene), where FIG. 6A is a top view and FIG. 6B is a side view. FIGS. 7A and 7B are photographic images showing a status of a droplet of hydrophilic reagent (aqueous reagent including surfactant Tween20) when placed on a substrate (having the uneven pattern) formed of PMP (polymethyl pentene), where FIG. 7A is a top view and FIG. 7B is a side view. The uneven pattern in FIGS. 7A and 7B is formed by arranging (at intervals vertically and horizontally) a plurality of protrusions in a shape of square column whose cross-section (bottom surface) is 800 μm by 800 μm square in shape. The interior angles of corners of the protrusion are all 90 degrees. FIGS. 6B and 7B show contact angles, where FIG. 6B shows a contact angle of 58 degrees when there is no uneven pattern and FIG. 7B shows a contact angle of 137 degrees when there is the uneven pattern, respectively.

As shown from the experimental results shown in FIGS. 6A, 6B, 7A and 7B, it can be seen that the contact angle of the droplet placed on the uneven pattern becomes larger. The function of the uneven pattern is not limited to the case where the uneven pattern is formed by arranging a plurality of protrusions in the shape of the column as shown in FIGS. 7A and 7B at intervals vertically and horizontally, but also shown in the case where linear protrusions 5_a_ such as those in Embodiment I are arranged at intervals so that the contact angle of the specimen passing through the movement path control region 5 becomes larger in the microchip 100_a_ of Embodiment I.

Figure 8:
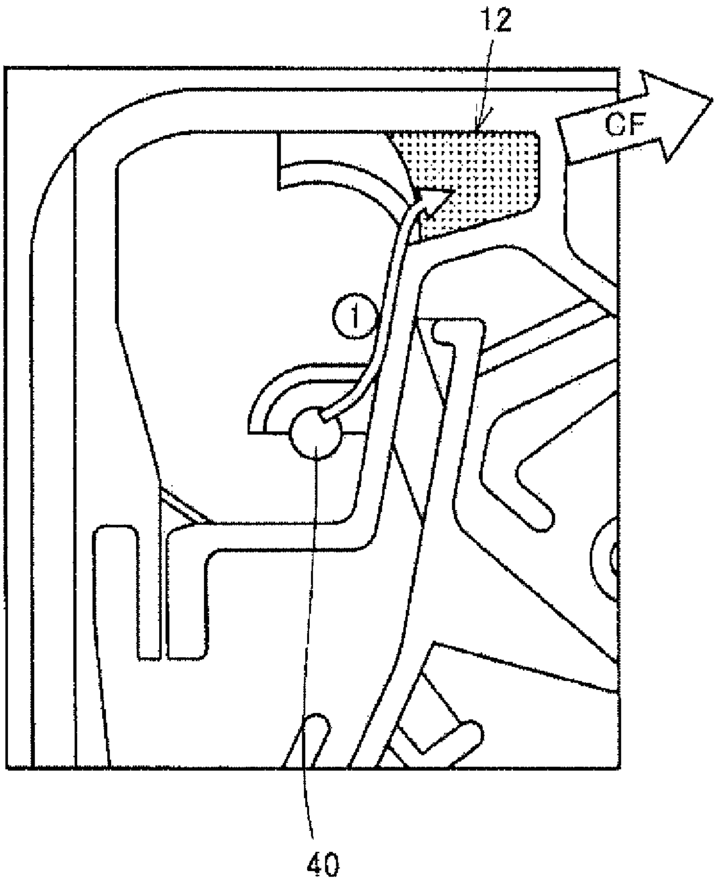
FIG. 8 is a top view showing a situation of introducing a specimen into a certain region of a second fluid circuit through a through-hole, according to some embodiments.
Figure 9:
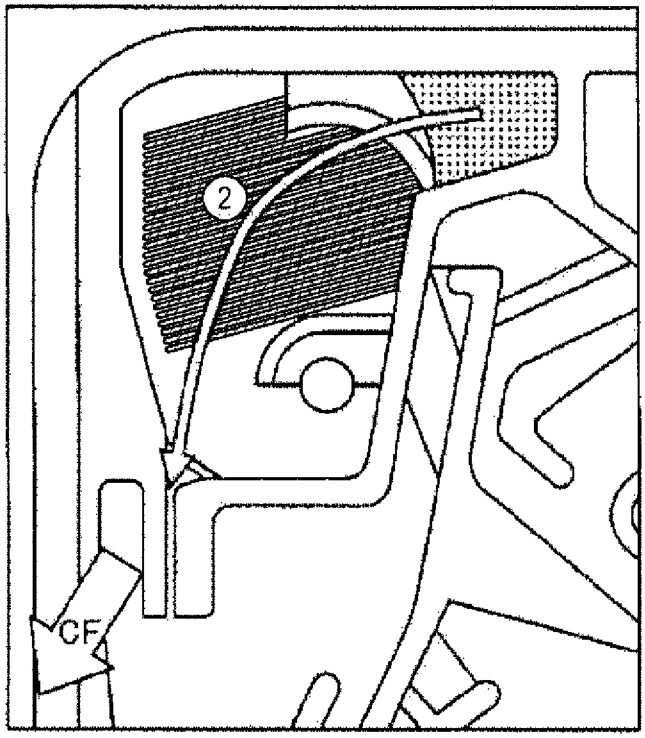
FIG. 9 is a top view showing a situation of moving a specimen from a certain region to a separation portion of a second fluid circuit in a microchip, according to some embodiments.
Figure 10:
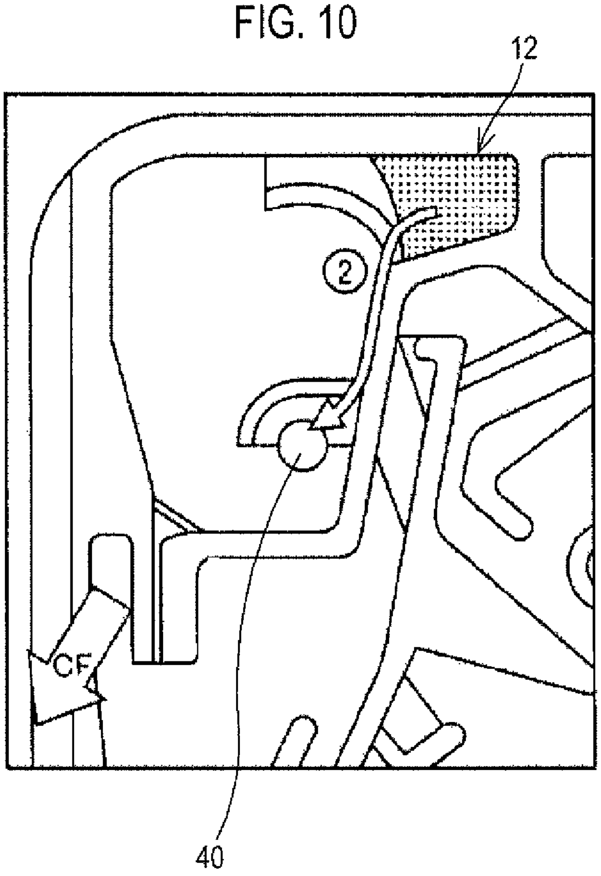
FIG. 10 is a top view showing a situation of moving a specimen from a certain region to a separation portion of a second fluid circuit in a conventional microchip having no movement path control region.

The control of the movement path of the specimen by the movement path control region 5 in the microchip 100_a_ of Embodiment I will be described in more detailed. FIG. 8 is a top view showing a process of introducing the specimen into the region 12 of the second fluid circuit through the through-hole 40 by the application of centrifugal force in a rightward direction of FIG. 3 (in a leftward direction of FIG. 2) (FIG. 8 shows the case where there is no movement path control region 5, but the microchip 100_a_ of Embodiment I includes the movement path control region 5, as shown in FIG. 9) (a first process). FIG. 9 is a top view showing a process of moving the specimen from the region 12 to the separation portion 501 by the application of centrifugal force in a downward direction of FIG. 3 in the microchip 100_a_ of Embodiment I (a second process). FIG. 10 is a top view showing a process of moving the specimen from the region 12 to the separation portion 501 by the application of centrifugal force in the downward direction of FIG. 3 in the conventional microchip which does not include the movement path control region 5 (a second process).

Any one of FIGS. 8 to 10 shows an enlarged area corresponding to the portion "A" shown in FIG. 3. "CF" in FIGS. 8 to 10 refers to the centrifugal force, and the arrow points to the direction of the centrifugal force. Referring to FIG. 8, when the centrifugal force is applied in the rightward direction with regard to the center of the microchip 100_a_, the centrifugal force in an approximate top-right direction is applied to the portion "A." In addition, referring to FIGS. 9 and 10, when the centrifugal force is applied in the downward direction with respect to the center of the microchip 100_a_, the centrifugal force in an approximate bottom-left direction is applied to the portion "A." Another arrow in FIGS. 8 to 10 shows the movement path of the specimen.

As shown in FIG. 10, it has been revealed that the specimen is not moved through a path in parallel to the direction of the centrifugal force but moved through a path nearer to the through-hole 40 than the path in parallel to the direction of the centrifugal force (the path 2 shown in FIG. 10) in the conventional microchip, when the centrifugal force is applied in the downward direction (approximately in the bottom-left direction in the portion "A") in the second process. This is because a wettability of the specimen with respect to the substrate surface (the inner surface of the fluid circuit) is high (the contact angle is small) so that the specimen tends to flow along the intersection between the bottom surface and the side surface of the fluid circuit. In case of taking such a path, a portion of the specimen may flow back into the through-hole 40 during the second process in the conventional microchip.

In contrast, the movement path control region 5 is provided in the microchip 100_a_ of Embodiment I so that the specimen is moved through a path (the path 2 shown in FIG. 9) farther from the through-hole 40 than the path in parallel to the direction of the centrifugal force, as shown in FIG. 9, when the centrifugal force is applied in the downward direction (approximately in the bottom-left direction in the portion "A") in the second process. Such an improvement in the movement path of the specimen is caused by the function of the above-mentioned uneven pattern. More specifically, the movement path of the specimen is improved because the movement of the specimen based on the centrifugal force becomes dominant while the movement based on the wettability (surface tension) of the specimen is suppressed by the increase of the contact angle.

If the movement path control region 5 is formed of an array of linear protrusions as shown in Embodiment I, the liquid tends to flow along the longitudinal direction of the linear protrusions when the centrifugal force is applied. This is why the path which is more deviated to the left side of FIG. 9 (such as the path 2 shown in FIG. 9) than the path in parallel to the direction of the centrifugal force is taken at the second process in the microchip 100*a* of Embodiment I. A degree of deviation (of the path) from the direction parallel to the direction of the centrifugal force can be controlled by adjusting an angle of the longitudinal direction of the linear protrusion with respect to the direction of the centrifugal force. In this manner, when the movement path needs to be controlled so that the liquid can pass through the path different from that in the direction parallel to the direction of the centrifugal force, the angle $\alpha$ between the direction of the centrifugal force and the longitudinal direction of the linear protrusion may be advantageously more than 0 but less than 90 degrees (the angle $\alpha$ may be a minimum of 0 and a maximum of 90 degrees).

On the other hand, when the movement path needs to be controlled so that the liquid can pass through the path in the direction parallel to the direction of the centrifugal force, the angle $\alpha$ between the direction of the centrifugal force and the longitudinal direction of the linear protrusion may be 0 degrees (that is, those two directions are in parallel).

When the movement path control region 5 is formed of the array of linear protrusions as in Embodiment I, a width of the linear protrusion may be, for example, 10 to 1000 μm, or 50 to 200 μm in order to facilitate the function of increasing the contact angle of the liquid. In addition, a pitch between the linear protrusions can be, for example, 10 to 1000 μm or 50 to 200 μm. Generally, a height of the linear protrusion may be 50 to 300 μm. However, the height of the linear protrusion is not limited thereto since it does not affect the contact angle of the liquid significantly.

The smaller R of the corner of the linear protrusion (the corner is formed by a top surface and a side surface of the protrusion) is, the more the contact angle increases. R of the corner may be 50 μm or less, or alternatively 10 μm or less. The same applies to other types of the uneven pattern.

Though the movement path control region 5 may be formed in any position of the inner surface of the fluid circuit, it is generally formed on an inner surface of the flow path connecting between the portions (chambers) as in Embodiment I, especially on an inner surface of the flow path where a problem may occur for a predetermined fluid treatment if the liquid moves through an unintended path. An area of the movement path control region 5 formed on such an inner surface is determined depending on a desired degree of the change of the movement path of the fluid. The linear protrusions may be provided over a region ranging from the side surface of the region 12 constituting the flow path to at least the path 2 shown in FIG. 9 in order to regulate the path 2 shown in FIG. 10 to the path 2 shown in FIG. 9 in Embodiment I. In case of moving the liquid in the fluid circuit from a region A to a region B by the application of the centrifugal force, the movement path control region 5 usually includes at least a portion of the region (flow path) interposed between the region A and the region B.

The movement path control region 5 may be provided on the bottom surface or the top surface (ceiling) opposite thereto in the inner surface of the fluid circuit, so that a good controllability of the movement path can be obtained. In some embodiments, the movement path control region 5 is provided on the bottom surface, since it can be formed at the same time as the grooves (fluid paths) constituting the fluid circuit when the substrate is molded, thus causing no positional deviation from the grooves.

Figure 11:
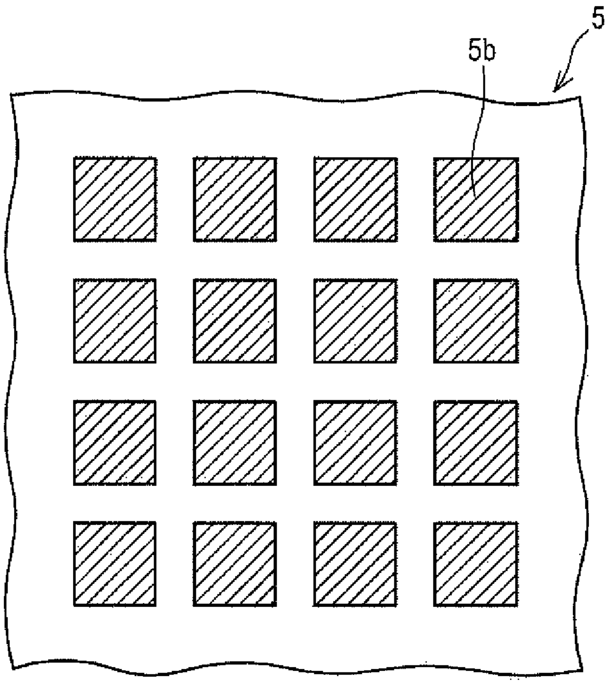
FIG. 11 is a top view showing another example of an uneven pattern constituting a movement path control region, according to some embodiments.
Figure 12:
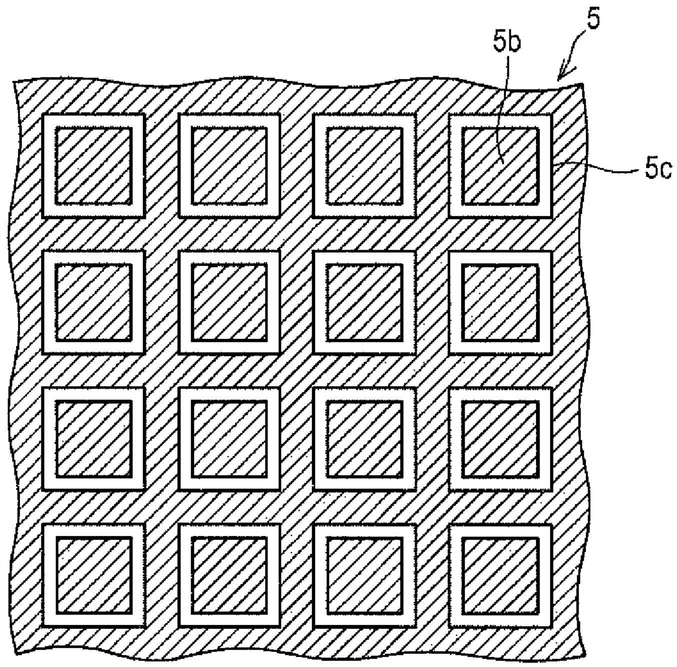
FIG. 12 is a top view showing still another example of an uneven pattern constituting a movement path control region, according to some embodiments.

The uneven pattern constituting the movement path control region 5 is not limited to the pattern consisting of the linear protrusions, but may include various patterns. FIGS. 11 and 12 are top views showing other examples of the uneven pattern in the movement path control region 5. Areas indicated by hatched lines refer to portions more protruding than those not indicated by hatched lines in FIGS. 11 and 12.

The movement path control region 5 shown in FIG. 11 consists of a plurality of columnar protrusions 5*b* arranged at intervals vertically and horizontally. The shape of a cross-section (bottom surface) of the protrusion 5*b* is not limited to a square shape as shown in FIG. 11, but may be another quadrangular shape such as a rectangular shape and a rhomboidal shape, a polygonal shape other than the quadrangular shape, a circular shape, an oval shape and so forth.

When the movement path control region 5 consists of a plurality of columnar protrusions 5*b* arranged at intervals vertically and horizontally as shown in FIG. 11, a cross-sectional diameter of the columnar protrusion 5*b* (a maximum distance between opposite sides in case of the polygonal shape or a length of the major axis in case of the oval shape; the same applies hereafter) may be 10 to 2000 μm or may be 100 to 1000 m, for example, so as to facilitate the function of increasing the contact angle of the fluid. In addition, a pitch between the columnar protrusions 5*b* may be 10 to 1000 μm or may be 100 to 500 μm, for example. Generally, the height of the columnar protrusion 5*b* may be 10 to 200 μm. However, the height of the columnar protrusion 5*b* is not limited thereto since it does not affect the contact angle of the liquid significantly.

The movement path control region 5 shown in FIG. 12 consists of a plurality of trenches 5*c* arranged at intervals horizontally and vertically so as to surround a portion of the inner surface of the fluid circuit (the region of the protrusion 5*b* in FIG. 12). More specifically, the movement path control region 5 shown in FIG. 12 consists of a plurality of frame-like trenches 5*c* arranged at intervals horizontally and vertically. The shape of the trenches 5*c* (therefore, the shape of a cross-section (bottom surface) of the protrusion 5*b*) is not limited to the square shape as shown in FIG. 12, but may be another quadrangular shape such as a rectangular shape and a rhomboidal shape, a polygonal shape other than the quadrangular shape, a circular shape, an oval shape and so forth.

When the movement path control region 5 consists of a plurality of trenches 5*c* arranged at intervals horizontally and vertically so as to surround a portion of the inner surface of the fluid circuit as shown in FIG. 12, the cross-sectional diameter of the columnar protrusion 5*b* surrounded by the trenches 5*c* may be 10 to 2000 μm or may be 100 to 1000 μm, for example, so as to facilitate the function of increasing the contact angle of the fluid. The width of the trenches 5*c* may be 10 to 1000 μm or may be 100 to 500 μm, for example. In addition, a pitch between the trenches 5*c* may be 10 to 2000 μm or may be 100 to 1000 μm, for example. Generally, the height of the columnar protrusion 5*b* (a depth of the trench 5*c*) may be 10 to 200 μm. However, the height of the columnar protrusion 5*b* is not limited thereto since it does not affect the contact angle of the liquid significantly.

In the following description, the examination and analysis method (fluid treatment operation) of the specimen (for example, whole blood) by the microchip 100*a* of Embodiment I will be described with regard to the "section 4".

(1) Introducing Whole Blood and Measuring Liquid Reagent

The whole blood is introduced from the specimen introduction hole 105 of the first substrate 1, and the centrifugal force is applied approximately in the downward direction of FIG. 2. This will cause the whole blood to be introduced into the receiving portion 801 through the region 10 (see FIG. 2). In addition, the liquid reagent in the reagent retaining portion 201*a* and the liquid reagent in the reagent retaining portion 211*a* are moved, respectively, through the reagent exhausting passages 202*a* and 212*a* to the reagent measuring portions 301*a* and 311*a*, then measured, by the application of centrifugal force approximately in the downward direction (see FIG. 3). The liquid reagent overflowing out of the reagent measuring portions 301*a* and portion 311*a* are received in the excess liquid storing portions 701 and 710 through the through-holes 20 and 30, respectively (see FIG. 2).

(2) Centrifugation

Thereafter, the whole blood is moved through the through-hole 40 to the region 12 by the application of centrifugal force approximately in the leftward direction of FIG. 2 (see FIG. 3). Subsequently, the whole blood in the region 12 is introduced into the separation portion 501 by the application of centrifugal force approximately in the downward direction of FIG. 3 (see FIG. 3). In succession, the centrifugation is performed in the separation portion 501 to separate a blood plasma component (upper layer) and a blood cell component (lower layer) by the application of centrifugal force approximately in the downward direction.

For each of 30 units of the microchips 100*a* including the movement path control region 5 and 30 units of the conventional microchips having the same structure as the microchip 100*a* except that they do not include the movement path control region 5, the whole blood in the region 12 was introduced into the separation portion 501 by the application of centrifugal force approximately in the downward direction (rotation speed: 3000 rpm), and the incidence of a back flow to the through-hole 40 as shown in FIG. 10 was calculated. The result shows that the incidence is 0% for the microchip 100*a* of the present embodiment and 43% (13 out of 30 units) for the conventional microchip.

(3) Measuring the Specimen

Thereafter, the centrifugal force is applied approximately in the rightward direction of FIG. 3. Thus, the blood plasma component separated in the separation portion 501 is introduced into the specimen measuring portion 401 (and introduced to other 5 specimen measuring portions at the same time), then measured (FIG. 3). The blood plasma component overflowing out of the specimen measuring portion 401 is moved through the through-hole 50 to the first fluid circuit (see FIG. 2). The liquid reagent in the reagent measuring portion 301*a* is moved to the mixing portion 900 and the liquid reagent in the reagent measuring portion 311*a* is moved to the region 11 by the application of centrifugal force approximately in the rightward direction.

(4) First Mixing

Thereafter, the centrifugal force is applied approximately in the downward direction of FIG. 3. Thus, the measured liquid reagent (the liquid reagent retained in the reagent retaining portion 201*a*) and the blood plasma component measured in the specimen measuring portion 401 are mixed in the reagent measuring portion 301*a* (a first step of the first mixing; see FIG. 3). Then, the mixed liquid is further mixed with the liquid reagent existing in the mixing portion 900 by the application of centrifugal force approximately in the rightward direction of FIG. 3 (a second step of the first mixing; see FIG. 3). The mixing can be performed more reliably by performing the first step and the second step several times as necessary.

(5) Second Mixing

Thereafter, the centrifugal force is applied approximately in the upward direction of FIG. 3. Thus, the mixed liquid in the mixing portion 900 is moved through the through-hole 60 to the mixing portion 910 and mixed with another measured liquid reagent (liquid reagent retained in the reagent retaining portion 211*a*) that is also moved through the through-hole 60 to the mixing portion 910 (a first step of the second mixing; see FIGS. 2 and 3). Then, the mixed liquid is moved within the mixing portion 910 so as to facilitate the mixing by the application of centrifugal force approximately in the rightward direction of FIG. 2 (a second step of the second mixing; see FIG. 2). The mixing can be performed more reliably by performing the first step and the second step several times as necessary.

(6) Introducing into the Detection Portion

Finally, the centrifugal force is applied approximately in the downward direction of FIG. 2. Thus, the mixed liquid in the mixing portion 910 is introduced into the detection portion 601. The mixed liquid in the detection portion 601 is subject to the optical measurement, and the examination and analysis of the specimen (blood plasma component) is performed. For example, the specific component in the mixed liquid is detected by irradiating with light approximately perpendicular to the surface of the microchip 100*a* and measuring the transmitted light. The same applies to the mixed liquid introduced into another detection portion.

According to the microchip 100*a*, the movement path control region 5 is provided on the inner surface of the fluid circuit and a movement path of liquid can be controlled properly so that the liquid can move along an intended path while preventing the liquid from moving through an unintended path when centrifugal force is applied to move the liquid, thus preventing the liquid from moving to an unintended position in the fluid circuit. This improves an accuracy and a reliability of the examination and analysis by the microchip 100*a*.

Further, the uneven pattern formed in the movement path control region 5 can be provided simultaneously with the formation of the grooves forming the fluid circuit on the substrate by an injection molding using a mold. Thus, the microchip 100*a* can be produced easily without complicating the manufacturing process.

While certain embodiments have been described, these embodiments have been presented by way of example only, and are not intended to limit the scope of the disclosures. Indeed, the novel methods and apparatuses described herein may be embodied in a variety of other forms; furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A microchip having a fluid circuit defined by a space formed in the microchip and configured to move a liquid present in the fluid circuit from a first position to a second position in the fluid circuit by applying a centrifugal force in a predetermined direction, the microchip comprising:

a first liquid retaining portion including a first opening through which the liquid is discharged, and containing the liquid;

a second opening disposed at a first position towards a first direction, to which the centrifugal force is applied, with respect to the first opening;

a second liquid retaining portion disposed at a second position towards the first direction with respect to the second opening, and including a third opening through which the liquid is received from the first liquid retaining portion;

a protrusion portion, extending from the first opening in a second direction perpendicular to the first direction beyond an edge of the second opening, configured to divert the liquid from the second opening and to prevent back flow of the liquid to the second opening at the time the centrifugal force is applied; and a flow path connecting the first and second retaining portions past the second opening.

2. The microchip of claim 1, wherein the protrusion portion is provided on the bottom surface of the fluid circuit.

3. The microchip of claim 1, wherein the protrusion portion includes a plurality of linear protrusions arranged in parallel at intervals.

4. The microchip of claim 1, wherein the protrusion portion includes a plurality of protrusions arranged in the first direction.

5. The microchip of claim 1, wherein the protrusion portion is formed to incline more towards the first direction than the second direction.

6. The microchip of claim 1, wherein the microchip is formed by sequentially stacking and bonding a first substrate, a second substrate having grooves on both surfaces of the second substrate, and a third substrate, wherein the fluid circuit comprises:

a first fluid circuit formed by a surface of the first substrate facing the second substrate and the grooves on a surface of the second substrate facing the first substrate; and a second fluid circuit formed by a surface of the third substrate facing the second substrate and the grooves on a surface of the second substrate facing the third substrate.

7. The microchip of claim 6, wherein the first fluid circuit includes the first and second liquid retaining portion, and wherein the second opening penetrates through the second substrate and connects the first fluid circuit and second fluid circuit.

8. The microchip of claim 1, wherein the second and third openings are sequentially arranged on an opposite side from the second direction with respect to the first opening.

9. The microchip of claim 1, wherein the liquid includes a whole blood sample, and the second liquid retaining portion is configured to separate the liquid into a blood plasma component and a blood cell component.

10. The microchip of claim 2, wherein the protrusion portion is arranged such that the liquid passes over the protrusion portion.

* * * * *